United States Patent
Wyman

Patent Number: 5,868,997
Date of Patent: Feb. 9, 1999

[54] STERILIZATION OF FERMENTATION VESSELS BY ETHANOL/WATER MIXTURES

[75] Inventor: Charles E. Wyman, Lakewood, Colo.

[73] Assignee: Midwest Research Institute, Kansas City, Miss.

[21] Appl. No.: 672,286

[22] Filed: Mar. 20, 1991

[51] Int. Cl.[6] .......................................... A61L 2/18
[52] U.S. Cl. .................. 422/28; 422/27; 422/31; 422/32; 422/33; 426/9; 426/532; 426/592
[58] Field of Search .................................. 422/27, 28, 31, 422/32, 33; 426/9, 532, 592

[56] References Cited

U.S. PATENT DOCUMENTS

| | | |
|---|---|---|
| 903,853 | 11/1908 | Gartner . |
| 3,908,031 | 9/1975 | Wistreich et al. . |
| 3,997,400 | 12/1976 | Heden . |
| 4,287,303 | 9/1981 | Dahlberg et al. . |
| 4,413,058 | 11/1983 | Arcuri et al. . |
| 4,431,838 | 2/1984 | Feldman et al. .................. 203/DIG. 6 |
| 4,510,242 | 4/1985 | Tedder . |
| 4,808,526 | 2/1989 | Lawford . |
| 4,845,033 | 7/1989 | Tegtmeier . |
| 5,167,937 | 12/1992 | Harandi et al. .................. 203/DIG. 6 |

*Primary Examiner*—Timothy McMahon
*Attorney, Agent, or Firm*—Ken Richardson

[57] ABSTRACT

A method for sterilizing process fermentation vessels with a concentrated alcohol and water mixture integrated in a fuel alcohol or other alcohol production facility. Hot, concentrated alcohol is drawn from a distillation or other purification stage and sprayed into the empty fermentation vessels. This sterilizing alcohol/water mixture should be of a sufficient concentration, preferably higher than 12% alcohol by volume, to be toxic to undesirable microorganisms. Following sterilization, this sterilizing alcohol/water mixture can be recovered back into the same distillation or other purification stage from which it was withdrawn. The process of this invention has its best application in, but is not limited to, batch fermentation processes, wherein the fermentation vessels must be emptied, cleaned, and sterilized following completion of each batch fermentation process.

21 Claims, 1 Drawing Sheet

STERILIZATION OF FERMENTATION VESSELS BY ETHANOL/WATER MIXTURES

CONTRACTUAL ORIGIN OF THE INVENTION

The United States Government has rights in this invention under Contract No. DE-AB01-89GC20195.M000 between the U.S. Department of Energy and the Solar Energy Research Institute, a Division of Midwest Research Institute.

BACKGROUND OF THE INVENTION

1. Field of the Invention

The present invention relates generally to sterilization of vessels, and more specifically to the sterilization of fermentation vessels used for the production of aqueous solutions of ethanol.

2. Description of the Prior Art

Aqueous solutions of ethyl alcohol, or ethanol, are produced by microorganisms, such as yeast, from sugars derived from such crops as sugar cane or by enzymatic transformation of starch or cellulose in biomass to form sugars for alcoholic fermentation. In the latter fermentation processes, starch-containing crops or cellulosic biomass, which contains lignin, cellulose, and hemicellulose, is first broken down in water by enzymatic or acid hydrolysis into sugars, such as glucose or xylose. Yeast microorganisms then consume these sugars, converting them into an aliphatic alcohol, such as ethanol. In industrial alcohol production facilities, this entire process, or at least its final stages, occur in large fermentation vessels.

If these fermentation vessels are not properly disinfected or sterilized between batches or uses, bacteria and other undesirable microorganisms can become attached to the interior walls of the fermentation vats where they will grow and flourish. These undesirable microorganisms may contaminate ethanol co-products such as animal feed, or they may consume valuable quantities of the substrate, or sugar, thus reducing the production of ethanol. The economics and efficiency of fermentation processes are frequently such that they cannot tolerate any such loss of production.

Current methods used to kill these unwanted microorganisms often involve introduction of foreign agents, such as antibiotics, heat, and strong chemical disinfectants, to the fermentation before or during production of ethanol. The addition of each of these foreign agents to the process significantly adds to the time and costs of ethanol production. Antibiotics are very expensive and can add greatly to the costs of a large-scale production. The use of heat requires substantial energy to heat the fermentation vessels as well as possibly requiring the use of special, pressure-rated vessels that can withstand the high temperatures and pressures generated in such heat sterilizing processes. Chemical treatments can also add to the cost of production due primarily to the cost of the chemicals themselves and secondarily to the fact that these chemicals are often hazardous materials requiring special handling and environmental and safety precautions.

While the efforts in the ethanol production industry to sterilize and disinfect fermentation vessels have been focused almost exclusively on the use of such costly and hazardous chemicals, as described above, there has been very little thought given or efforts directed to an effective and efficient use of ethanol itself as a disinfectant in the ethanol production process, even though the effectiveness of ethanol as a disinfectant for other purposes has been long-known. For example, U.S. Pat. No. 903,853, issued to G ärtner back in 1908, described the use of a heated aqueous solution of ethanol or methanol to disinfect books, including a solution of 100 parts 96% alcohol and 80 parts water. U.S. Pat. No. 3,908,031, issued to Wistreich et al. on Sep. 23, 1975, similarly describes using ethanol in the vapor phase to sterilize food products and spices, including a concentration of ethanol in water that was at least 80% by volume and at least 78° C., but preferably 150° C. in order to prevent condensation of the ethanol vapor on the food products or spices.

Heden, in his U.S. Pat. No. 3,997,400, describes the use of unheated, concentrated alcohol in conjunction with a strong chemical, such as betapropiolactone, to sterilize the interior walls of the tanks of an oil tanker so that they might be used as fermentation vessels to produce yeast fodder for cattle feed when the tanks are not being used to haul oil.

Tegtmeier, in his U.S. Pat. No. 4,845,033, attempted to take advantage of the somewhat higher alcohol, pH, and temperature tolerance of yeast over some other microorganisms to minimize such other microorganisms in a continuous alcohol production process. Tegtmeier used a two-stage continuous process to do so. In his first stage, Tegtmeier provides a good nutritional, oxygen, and growing environment for desirable alcohol producing yeast microorganisms to get a healthy population and good cell sizes of those desirable microorganisms for use in his second stage to produce alcohol while controlling pH, oxygen, and temperature operating parameters to discourage undesirable microorganisms. Tegtmeier also keeps the alcohol concentration in his second stage higher than most undesirable microorganisms can tolerate. Therefore, undesirable microorganisms produced in the first stage and injected along with the desirable yeast microorganisms into the second stage have difficulty thriving in the second stage. Unfortunately, the desirable yeast microorganisms, while surviving, are stressed and not as vigorous or healthy in that high alcohol concentration either, so they do not perform as well as they could in a lower alcohol concentration, and alcohol production suffers. However, Tegtmeier's process accepts this trade-off of reduced production capability of the desirable alcohol producing microorganisms for the benefit of reducing the undesirable microorganism population in his second or production stage.

Consequently, there is still much to be desired in the field of ethanol production, particularly in batch production processes, for effective fermentation vessel sterilization that is also safe, low cost, and environmentally sound, yet which enhances, rather than degrades or limits efficient alcohol producing microorganism activity.

SUMMARY OF THE INVENTION

Accordingly, a general object of the present invention is to provide a safe, clean, fast, easy, and economical method of sterilizing fermentation vessels, which includes recovery of any usable material.

Another general object of this invention is to provide a method of complete sterilization of fermentation vessels, which does not interfere with the actual production from the fermentation vessels.

Another object of this invention is to provide a quick and easy method of completely disinfecting and sterilizing fermentation vessels used in an ethanol production process, which neither significantly adds to the production costs nor limits production and overall efficiency.

Another more specific object of the present invention is to provide an effective and efficient method and apparatus for utilizing ethanol as produced in an ethanol production process to disinfect and sterilize the fermentation vessels used in the process and then recover this same concentrated ethanol back into the production process.

Additional objects, advantages, and novel features of the invention shall be set forth in part in the description that follows, and in part will become apparent to those skilled in the art upon examination of the following or may be learned by the practice of the invention. The objects and the advantages of the invention may be realized and attained by means of the instrumentalities and in combinations particularly pointed out in the appended claims.

To achieve the foregoing and other objects and in accordance with the purpose of the present invention, as embodied and broadly described herein, the method of this invention may comprise sterilizing a fermentation vessel with concentrated alcohol contained in an aqueous solution. The alcohol utilized in this method is preferably alcohol that has been produced by the production facility or may even have been fermented in the very vessel it sterilizes.

The alcohol in an aqueous solution should be of a sufficient concentration to be toxic to undesirable microorganisms, thereby providing a faster, more efficient, and more complete sterilization. This concentration should be at least 12% alcohol by volume, but may be higher such as 40% to 60% alcohol-in-water, including almost pure alcohol at 90% to 95% alcohol-in-water. Alcohol at a wide variety of concentrations can easily be drawn from a distillation or other purification process associated with the alcohol production process.

This concentrated alcohol in aqueous solution may additionally be heated, up to and including the boiling point of the alcohol. This should increase the overall speed and effectiveness of the disinfection and sterilization process. Once again, such hot, concentrated, alcohol and water mixture, or even vapor alone, can be withdrawn easily from a distillation facility commonly associated with ethanol production plants.

In a batch fermentation processes the fermentation vessel must be emptied, cleaned, and sterilized following completion of the fermentation process. Continuous fermentation vessels are also emptied periodically between campaigns or for maintenance. Following the emptying and cleaning of the fermentation vessel, this concentrated and possibly heated sterilizing solution of alcohol and water may be introduced into the vessel. This concentrated ethanol may additionally be sprayed into the fermentation vessel to provide more complete coverage of the interior walls of the fermentation vessel. If as described above, the sterilizing alcohol is heated up to or near its boiling point, this spray of alcohol may contain water and partially or totally gaseous alcohol. This gaseous alcohol will condense on the interior walls of the fermentation vessels, providing perhaps even more complete sterilization and disinfection.

BRIEF DESCRIPTION OF THE DRAWINGS

The accompanying drawings, which are incorporated herein and form a part of the specification, illustrate preferred embodiments of the present invention, and together with the description, serve to explain the principles of the invention. In the drawings.

DETAILED DESCRIPTION OF THE PREFERRED EMBODIMENTS

Figure 1:
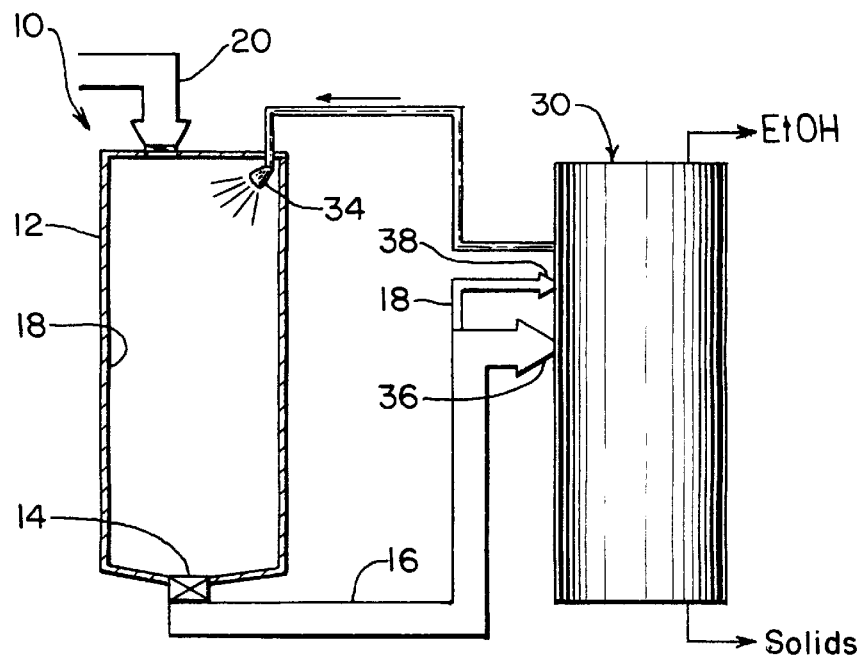
FIG. 1 is a schematic layout of a batch fermentation process with an integrated alcohol sterilization process in accordance with the preferred embodiment of the present invention.

An integrated alcohol production facility 10 according to this invention is shown in FIG. 1. It uses a batch alcoholic fermentation process, water, some form of biomass, enzymes and an alcohol producing organism, such as yeast, placed in a fermentation vessel 12. The yeast then produces alcohol in fermentation vessel 12 through metabolic conversion of the biomass in a process known as alcoholic fermentation. Following the alcoholic fermentation, vessel 12 is emptied by a drainage valve 14 and delivered to a distillation facility 30 by a liquid and solid carrying conduit 16. In brief, distillation facility 30 operates by separating the solids and water from the liquid alcohol portion of the fermentation. The distillation facility 30 further purifies or concentrates the alcohol constituent of the liquid portion, possibly even to the point of producing pure ethanol.

Once emptied, fermentation vessel 12 has to be cleaned and sterilized before the next batch is introduced in order to kill undesirable microorganisms that may consume valuable biomass during later fermentations without producing alcohol. Such undesirable microorganisms if not killed, could even contaminate co-products produced during later fermentations. Therefore, according to the present invention, a hot, concentrated, solution of alcohol and water can be drawn from distillation facility 30 and returned to the now empty and clean fermentation vessel 12 via conduit 32 and spray nozzle 34 or other means. This hot, concentrated mixture of water and alcohol is sprayed through nozzle 34 into the interior of vessel 12 to sterilize it. This concentrated mixture is a very effective sterilizing agent because the alcohol content or concentration coming out of the distillation facility 30 is concentrated or pure enough, usually well above the maximum twelve percent (12%) purity of alcohol produced in the fermentation vessel 12, so that it is very toxic to most microorganisms. Spraying this concentrated alcohol solution not only ensures more complete coverage of interior surfaces 18, but, when the alcohol solution is hot, it enhances flashing and vaporization of the alcohol to accomplish a more complete sterilization of the interior of vessel 12. While it is not known for sure what actually causes this effect of greater sterilization, the higher temperature of the alcohol probably helps, and the vapor probably provides a more pervasive transport mechanism carrying the alcohol to virtually the entire interior surface and to virtually every exposed microorganism in the vessel 12. This alcohol vapor might then condense on the exposed microorganisms, or it might simply move through the cell walls or some other mechanism at work.

It is also possible to remove the alcohol/water mixture from the distillation facility 30 at a point in the process that the alcohol is in the vapor state, or it can be removed where it is a hot enough liquid to flash, as described above, or, if it is too cool to flash, a heating mechanism (not shown) can be placed in conduit 32. If the concentrated alcohol/water mixture is already in vapor form when it is introduced into vessel 12, spray nozzle 34 may be replaced by a regular inlet nozzle (not shown). Additionally, with the use of alcohol vapor, there is a sufficient temperature gradient between the alcohol vapor and fermentation vessel 12 that the vapor should condense on the interior walls 18 and kill any microorganisms on the walls, and possibly even wash them to the bottom of the vessel 12 where they can be removed.

Once fermentation vessel 12 has been sterilized, this used sterilizing solution of concentrated alcohol and water can be removed from vessel 12 by the same conduit 16 that is used to remove the original fermentation liquids and solids, and it can likewise be returned to distillation facility 30. This sterilizing solution may be returned to distillation facility 30 either at the same inlet port 36 as the initially fermented material is delivered or by an alternative branch conduit 18 to any desired place within distillation facility 30. For example, conduit branch 18 can be connected to return the sterilizing solution to any desired concentration of alcohol and water in the distillation facility 30, including the same concentration level from which it was originally removed for sterilizing vessel 12. The ethanol may also be left in the vessel and removed with subsequent product for recovery or processing by distillation or other means.

The advantages with the sterilization process of the present invention, as briefly outlined above, are many. First, the sterilization material used is of high quality, allowing quick, easy, and complete sterilization and disinfection of any undesirable microorganisms. High concentrations of alcohol are very toxic to microorganisms. Even the various yeast and other alcohol producing microorganisms can only tolerate concentrations to about 12% alcohol by volume.

Any conventional distillation or other purification process quickly generates concentrations well above the maximum alcohol concentration of 12% by volume that can be tolerated by most alcohol producing microorganisms, such as 40% to 60% alcohol-in-water mixture, or, for example, 50% alcohol, or 100 proof. In a fuel-alcohol production plant, alcohol concentrations of virtually 100% can be achieved. Fuel-alcohol is defined as any concentration at 95% or above. Accordingly, concentrations of 90% to 95% alcohol-in-water could also be used.

Second, this high quality sterilization material is inexpensive and easily available. In fact there is not much significant additional expense for the sterilizing solution of concentrated alcohol and water, since it is part of the process itself and, once used for sterilization purposes, is returned to the system from whence it came. Thus, the additional costs associated with the sterilization process are essentially only the pumping and delivery system, including conduit 32 and spray nozzle 34, as well as perhaps whatever additional energy is needed to reheat the alcohol solution for redistillation.

The third major advantage of this sterilization process of the present invention is that it can be accomplished quickly and effectively, without reducing alcohol production. This is accomplished, first by keeping the sterilization process separate from the alcohol producing fermentation process, despite using the same alcohol produced in that fermentation for the sterilization. By keeping the sterilization and fermentation processes separate, the yeast or other alcohol producing organisms are not unduly or unnaturally stressed by high alcohol concentrations into producing less alcohol. Even though the yeast can tolerate high concentrations of alcohol, up to about 12% by volume, they are adversely affected by alcohol concentrations approaching 12%, and their metabolism, thus the alcohol producing capability, is increasingly impaired as the alcohol concentrations approach 12%. Adding the sterilizing solution of alcohol and water as part of the fermentation process would limit alcohol production by stressing the yeast, if not outright killing the yeast, depending upon the concentration.

An additional way in which the process of the present invention accomplishes sterilization of alcohol fermentation vessels with an alcohol and water solution, but without reducing production, is through its recovery of the sterilizing alcohol back into the system. Accordingly, as much concentrated alcohol and water solution as is needed to sterilize a fermentation vessel 12 can be drawn off from the distillation facility 30 without fear of reduced production. Even though this sterilizing solution of alcohol and water contains dead microorganisms upon its return to the distillation or purification facility 30, there is not a real concern of "contamination" or dirtying of the alcohol and water solution. First, these microorganisms are now dead, and, second, the solution delivered to distillation facility 30 originally upon completion of the fermentation procedure usually contains microorganisms, i.e., the yeast or other alcohol producing microorganisms. In addition this fermentation solution, which is delivered to the distillation facility, usually contains residual enzymes, acids, and undigested biomass, such as lignin and possibly some leftover cellulose, hemicellulose, or even some starch or sugars. The distillation or purification process is not only to concentrate the alcohol in the water, but to separate out these residual solids, which also have economic worth, such as fodder yeast or distillers dry grains with solubles in the case of a dry milling fermentation process.

As described above, it is preferred that the alcohol and water solution used for sterilization be concentrated above 12% in order to effectively kill undesirable microorganisms. If unrecovered this sterilizing alcohol would be lost, and the use of increasingly higher concentrations of alcohol would result in increasingly higher losses of alcohol. However, because the alcohol can be recovered back into the system according to this invention, the threat of lost production need not be a factor, thus it does not limit the concentration selected as a sterilizing solution. One need only choose where in the distillation facility a concentrated solution of alcohol and water should be tapped and whether that concentration is high enough to be toxic in the time allowed for disinfection. As mentioned above, it is available in most conventional distilling processes up to and including pure alcohol, i.e., essentially 100% alcohol. The actual mechanism by which alcohol kills microorganisms involves the osmotic pressure within the liquid medium, which pressure increases as the alcohol concentration increases. As alcohol concentrations increase, the osmo-sensitive or alcohol-sensitive organisms become increasingly stressed. This osmotic pressure can become sufficiently great so as to begin destroying the microorganism's cell walls. When this occurs, the microorganism becomes overwhelmed or bloated with alcohol, essentially pickling the microorganism.

For purposes of illustration and not for limitation, fermentation vessel 12 is typically a large tank, for example, in the range of 300,000 gallons to about 650,000 gallons. The batch fermentation process of the present invention may be applied in either a wet or a dry milling process. In a dry milling fermentation process, water, a starchy grain, such as corn, and an enzyme or acid are used to break down the biomass, and yeast is delivered to fermentation vessel 12 by way of inlet main 20. The biomass has typically gone through an enzymatic hydrolysis, wherein the starch portion of the biomass is converted to glucose. Then the yeast, in the actual fermentation process, metabolically converts the sugar, glucose, to ethanol. For example, in a dry milling fermentation process one bushel of corn (47.32 lbs) produces about 2.6 gallons of ethanol, about 16–17 lbs of distillers dry grains with solubles, and about 16–17 lbs of carbon dioxide ($CO_2$).

The theoretical production of ethanol from the stoichiometry of this dry milling process is a little higher. The equation for the conversion of glucose into ethanol is:

$C_6H_{12}O_6 \rightarrow 2C_2H_5OH + 2CO_2$.

Accordingly, in theory each mole of glucose can be used to generate 2 moles of ethanol. This theoretical ideal of the production cannot be achieved in a real process because portions of the glucose substrate have to go into cell and population growth as well as cell maintenance of the mature yeast microorganisms.

In a wet milling process, the crude whole grain cellulosic biomass is broken down into starch and its other constituents prior to the actual fermentation process. Typically, enzymes break down in this starch to form glucose and water. The enzyme, the glucose, and yeast are then delivered to the fermentation vessel 12 by inlet main 20. The yeast then ferments the glucose into ethanol. An example of a typical wet milling fermentation process: one bushel of corn initially produces about 31.72 lbs of starch, 5.4 lbs fiber, 3.8 lbs corn steep liquor, 2.6 lbs corn gluten meal, 1.9 lbs corn oil, and 1.9 lbs germ meal. This 31.72 lbs of starch in turn produces about 2.5 gallons of ethanol.

Distillation and recovery facility 30 in a conventional ethanol production installation usually includes a beer still, a fractionation column, and an azeotropic distillation system (not shown). The beer still clarifies the fermentation liquors by removing cellulose, lignin, and other remaining biomass solids. As the name implies, the fractionation column fractionates the clarified liquor to produce an alcohol-water azeotrope. This alcohol-water azeotrope is then concentrated or separated in the azeotropic distillation system. In distillation, the alcohol-water azeotrope is heated, the vapors are collected, and then the vapors are condensed back into liquids. Because aliphatic alcohols have a lower boiling point than water, each such heating and recondensing results in solutions of water and alcohol that have progressively higher and higher concentrations of alcohol. For example, ethanol has a boiling point of about 70° C., as compared to the boiling point of water at about 100° C., at sea level. Such distillation and recovery facilities are commonly associated with fermentation vessels used for the production of distilled spirits and fuel-alcohol for the subsequent production of gasohol.

Figure 2:
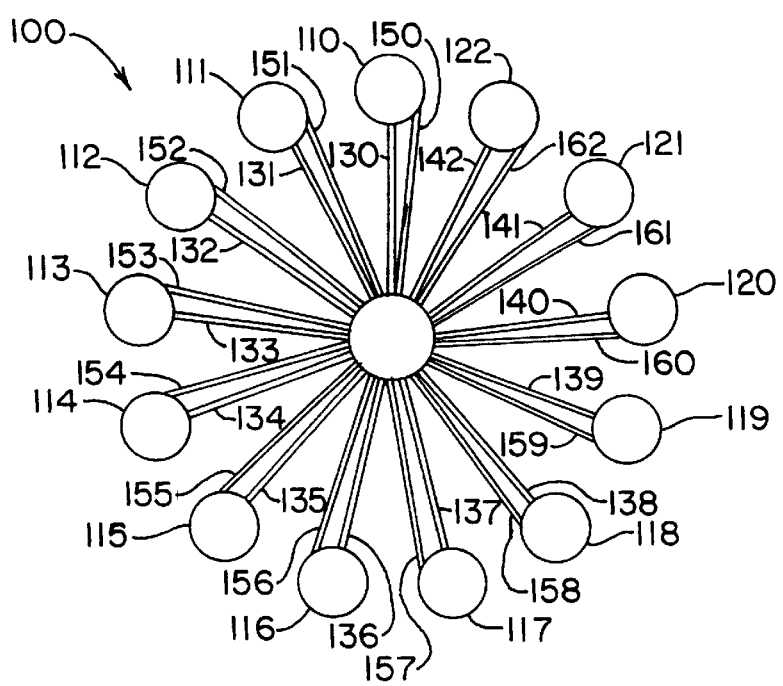
FIG. 2 is a plan view schematic of a multiple batch fermentation process with an integrated alcohol sterilization process in accordance with the preferred embodiment of the present invention.

In the integrated alcohol production facility 10, shown in FIG. 1, only a single batch fermentation vessel 12 is shown feeding the distillation facility 30. Typically there would be several batch fermentation vessels 12 feeding a single distillation facility 30 in a commercial-scale ethanol production facility. One such common arrangement of multiple fermentation vessels associated with a single distillation facility is illustrated in FIG. 2 as embodiment 100. Multiple fermentation vessel embodiment 100 includes thirteen fermentation vessels 110, 111, 112, 113, 114, 115, 116, 117, 118, 119, 120, 121, and 122, and a distillation facility 105, which are similar in construction and operation to the fermentation vessel 12 and distillation facility 30 described above with reference to embodiment 10. Each of these thirteen fermentation vessels has associated with them outlet conduits 130, 131, 132, 133, 134, 135, 136, 137, 138, 139, 140, 141, and 142, connecting each of the respective fermentation vessels to distillation facility 105. These outlet conduits are similar in nature and use to the liquid and solid conduit 16 described above. Each of these thirteen fermentation vessels also has associated with it a respective sterilization medium conduit 150, 151, 152, 153, 154, 155, 156, 157, 158, 159, 160, 161, and 162. These sterilization medium conduits are similar to conduit 32 described above, and they deliver a hot, concentrated, alcohol and water mixture from distillation facility 105 to each of the thirteen fermentation vessels, in turn, for the sterilization of them.

Thirteen fermentation vessels allow for continuous distillation, purification, and recovery at distillation facility 105, despite the batch nature of the fermentation process. With a 48 hour fermentation process, twelve of the fermentation vessels can be in different stages of the fermentation process, each separated in time by 4 hours, while one fermentation vessel is being cleaned and sterilized. For example, fermentation vessel 110 can be in the first 4 hours of the fermentation process, vessel 111 in the second 4 hours (or at 8 hours), vessel 112 at 12 hours, vessel 113 at 16 hours, and so on up to vessel 121, which will be in the final 4 hours (or at 48 hours). This leaves fermentation vessel 122 empty, to be cleaned and sterilized in accordance with the principles of the present invention, as described above.

Although the present invention has been described in most instances with a general reference to "alcohol," and an occasional specific reference to ethanol, the principles of the present invention are equally applicable to any common simple aliphatic alcohol.

The fermentation vessels primarily discussed in connection with the present invention have been for the fermentation of alcohol. However, the principles of the present invention are equally applicable to other fermentation processes and their associated fermentation vessels. For example the fermentation vessels used for the production of high fructose corn syrup by fermentation can be sterilized as described above with hot, concentrated alcohol/water mixtures. Such fructose production is frequently located in the same plant as an ethanol production facility, which would make the sterilizing alcohol and water mixture readily available.

Examples of suitable biomass substrates for the fermentation process include sugar-based materials, such as molasses, sugar cane, and sugar beets, and grains, such as corn, wheat, barley, rye, and oats. Cellulosic biomass containing primarily cellulose, hemicellulose, and lignin plus varying amounts of other materials may be used as well. Similarly, the fermenting microorganism employed in connection with the present invention can be any known microorganism used in fermentation processes, including various species of alcohol producing fungi known as yeast, thermophilic bacterium, and various strains of Zymomonas bacteria, which have recently received a great deal of attention. A typical fermentation temperature is preferably about 30° C. to 40° C., but may range from about 25° C. to 95° C.

Accordingly, a product and process have been provided that demonstrate a fast, safe, and efficient means of sterilizing fermentation vessels, using hot concentrated alcohol and water mixtures, which may be associated with the fermentation vessel to be sterilized. Additionally, the sterilization process of the present invention may be accomplished without significant production loss, due to the recovery of the concentrated alcohol and water solution back into the system.

The foregoing is considered as illustrative only of the principles of the invention. Further, since numerous modifications and changes will readily occur to those skilled in the art, it is not desired to limit the invention to the exact construction and operation shown and described, and accordingly all suitable modifications and equivalents may be resorted to falling within the scope of the invention as defined by the claims that follow.

The embodiments of the invention in which an exclusive property or privilege is claimed are defined as follows:

1. A method of sterilizing a fermentation vessel used in a batch fermentation process that includes an associated alcohol distillation or purification facility for purifying alcohol produced in the fermentation vessel to a higher alcohol concentration, wherein said fermentation vessel is intermittently emptied of fermented product, including alcohol, and cleaned, comprising the steps of:

withdrawing a sterilizing alcohol in aqueous solution from the distillation or purification facility with a sufficient concentration of alcohol to kill undesirable microorganisms;

sterilizing said emptied and cleaned fermentation vessel by introducing only said sterilizing alcohol in aqueous solution into the fermentation vessel;

withdrawing said sterilizing alcohol in aqueous solution from the fermentation vessel following the sterilization of said fermentation vessel and returning the sterilizing alcohol in aqueous solution to said distillation or purification facility.

2. The method of claim 1, wherein the emptied and cleaned fermentation vessel is used for the fermentation of alcohol.

3. The method of claim 1, wherein the emptied and cleaned fermentation vessel is used for the fermentation of products other than alcohol.

4. The method of claim 1, wherein the sterilizing alcohol in aqueous solution is heated to near the alcohol's boiling point.

5. The method of claim 1, wherein the step of introducing the alcohol in aqueous solution further comprises spraying the alcohol in aqueous solution into the fermentation vessel.

6. The method of claim 1, including the steps of leaving said sterilizing alcohol in said fermentation vessel after sterilizing the fermentation vessel, introducing a new batch of feedstock to be fermented into said fermentation vessel, allowing said feedstock to be fermented in said fermentation vessel to produce additional alcohol, and then withdrawing said sterilizing alcohol from the fermentation vessel and returning it to the distillation or purification facility along with the fermented feedstock and said additional alcohol.

7. In a batch alcohol producing process wherein successive batches of feedstock are placed sequentially into a fermentation vessel and fermented in the fermentation vessel by alcohol producing microorganisms to produce successive batches of a fermented mixture having a low alcohol concentration not exceeding about 12% alcohol by volume and wherein each successive batch of said fermented mixture is fed into a distillation process in which liquid containing alcohol in said mixture is distilled to a higher concentration alcohol/water solution exceeding 12% alcohol by volume and wherein the interior of the fermentation vessel is sterilized to kill undesirable microorganisms between successive batches, the improvement comprising the steps of:

withdrawing a portion of the alcohol containing liquid that has been distilled to an alcohol concentration above 12% alcohol content from the distillation process;

recirculating said withdrawn portion of alcohol containing liquid back into said fermentation vessel to sterilize the fermentation vessel and kill undesirable microorganisms in the fermentation vessel with only said withdrawn portion of alcohol containing liquid; and returning said withdrawn portion of alcohol containing liquid back into said distillation process.

8. The improvement of claim 7, including the step of spraying said withdrawn portion of alcohol containing liquid into the interior of said fermentation vessel.

9. The improvement of claim 7, including the step of spraying said withdrawn portion of alcohol containing liquid into said fermentation vessel at a temperature hot enough to enhance vaporization of the alcohol in the fermentation vessel.

10. The improvement of claim 7, including the step of spraying enough of said withdrawn portion of alcohol containing liquid into said fermentation vessel to substantially wash killed microorganisms off the interior walls of the fermentation vessel.

11. The improvement of claim 10, including the step of separating killed microorganisms from said alcohol containing liquid in the distillation process.

12. The improvement of claim 7, including the steps of distilling said alcohol/water solution to a plurality of successive stages of sequentially higher concentrations of alcohol, withdrawing said portion of alcohol containing liquid from one of said stages, and, after said recirculating step, returning said withdrawn portion of alcohol containing liquid back into substantially the stage of the distillation process from which it is withdrawn.

13. The improvement of claim 7, including the steps of distilling said alcohol/water solution to a plurality of successive stages of sequentially higher concentrations of alcohol, withdrawing said portion of alcohol containing liquid from one of said stages, and, after said recirculating step, returning said withdrawn portion of alcohol containing liquid back into the distillation process at a stage of the distillation process that precedes the stage from which it is withdrawn.

14. The improvement of claim 7, including the steps of introducing a new batch of feedstock into said fermentation vessel after said step of recirculating said withdrawn portion of alcohol containing liquid back into said fermentation vessel to sterilize and kill undesirable microorganisms, fermenting said new batch of feedstock to produce additional alcohol, and then returning said withdrawn portion of alcohol containing liquid back into said distillation process along with said fermented new batch of feedstock and said additional alcohol.

15. A process for producing alcohol, comprising the steps of:

placing a batch of fermentable feedstock or substrate in a fermentation vessel with water and alcohol producing fungi;

allowing the fungi to ferment the feedstock or substrate to produce a mixture having a liquid fraction comprising alcohol and water and a solid fraction comprising residual solid by-products of the fermentation process, with the alcohol and water in the liquid fraction having a concentration not exceeding an approximate maximum of twelve percent (12%) alcohol by volume;

removing the liquid and solid fractions from the fermentation vessel; separating the solid fraction from the liquid fraction;

distilling the liquid fraction to produce a higher purity alcohol product having an alcohol/water concentration of higher than twelve percent (12%) alcohol by volume;

withdrawing a portion of the higher purity alcohol from the alcohol product and spraying the withdrawn portion of the higher purity alcohol product into the fermentation vessel to sterilize the vessel with only said withdrawn portion of higher purity alcohol product;

collecting the withdrawn portion of the higher purity alcohol from the fermentation tank; and recombining the withdrawn portion with the higher purity alcohol product that was not withdrawn.

16. The process of claim 15, wherein the step of recombining the withdrawn portion with the higher purity alcohol product includes repeating the steps of separating solid fraction from liquid fraction and distilling the liquid fraction.

17. The process of claim 16, wherein the step of recombining the withdrawn portion with the higher purity alcohol product includes the steps of initially leaving the withdrawn portion in the fermentation vessel, adding a second batch of feedstock or substrate, water, and alcohol producing fungi to the fermentation vessel, fermenting the second batch, to produce additional liquid fraction comprising alcohol and water and additional solid fraction, and adding said additional liquid fraction and additional solid fraction along with said withdrawn portion to said steps of separating the solid fraction from the liquid fraction and distilling the liquid fraction.

18. A process for producing alcohol, comprising the steps of:

placing a batch of fermentable feedstock or substrate in a fermentation vessel with water and alcohol producing fungi;

allowing the fungi to ferment the feedstock or substrate to produce a mixture having a liquid fraction comprising alcohol and water and a solid fraction comprising residual solid by-products of the fermentation process;

removing the liquid and solid fractions from the fermentation vessel;

separating the solid fraction from the liquid fraction;

purifying the alcohol in the liquid fraction to a higher purity alcohol/water mixture having a higher alcohol concentration than was produced by the fermentation step;

withdrawing a portion of the higher purity alcohol/water mixture; and spraying only said withdrawn portion of the higher purity alcohol/water mixture into the fermentation vessel in vapor form to sterilize the fermentation vessel.

19. The process of claim 18, including the step of raising the temperature and pressure of the higher purity alcohol and flash evaporating the higher purity alcohol into the fermentation vessel.

20. The process of claim 19, including the step of simultaneously raising the temperature and purifying the alcohol in the liquid fraction by distiling the alcohol in the liquid fraction.

21. The process of claim 19, including the steps of condensing said evaporated alcohol in said fermentation vessel and recovering the condensed alcohol by removing the condensed alcohol from the fermentation vessel and adding the removed condensed alcohol back into said separating and purifying steps.

* * * * *